(12) United States Patent
Russ

(10) Patent No.: US 10,987,400 B2
(45) Date of Patent: *Apr. 27, 2021

(54) METHODS FOR THE TREATMENT OF GLAUCOMA AND AGE-RELATED MACULAR DEGENERATION BY A PEPTIDE D-TRP-AIB

(71) Applicant: RAMOT AT TEL-AVIV UNIVERSITY LTD., Tel Aviv (IL)

(72) Inventor: Hermann Russ, Altendorf (CH)

(73) Assignee: RAMOT AT TEL-AVIV UNIVERSITY LTD, Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/699,662

(22) Filed: Dec. 1, 2019

(65) Prior Publication Data

US 2020/0085906 A1    Mar. 19, 2020

Related U.S. Application Data

(63) Continuation of application No. 15/353,863, filed on Nov. 17, 2016, now Pat. No. 10,525,097, which is a continuation of application No. 12/733,270, filed as application No. PCT/EP2008/006888 on Aug. 21, 2008, now abandoned.

(60) Provisional application No. 60/965,650, filed on Aug. 21, 2007.

(30) Foreign Application Priority Data

Oct. 2, 2007 (FR) .................. 07253904.2

(51) Int. Cl.
| | | |
|---|---|---|
| A61K 38/00 | (2006.01) | |
| C07K 4/00 | (2006.01) | |
| A61K 49/00 | (2006.01) | |
| A61K 38/07 | (2006.01) | |
| A61K 38/08 | (2019.01) | |
| A61K 9/00 | (2006.01) | |
| A61K 38/06 | (2006.01) | |
| A61K 45/06 | (2006.01) | |
| C07K 14/47 | (2006.01) | |
| C07K 5/078 | (2006.01) | |
| C07K 5/065 | (2006.01) | |
| A61K 38/05 | (2006.01) | |
| C07K 5/087 | (2006.01) | |
| A61B 3/10 | (2006.01) | |
| G06T 5/50 | (2006.01) | |
| A61B 3/12 | (2006.01) | |
| A61K 47/02 | (2006.01) | |
| A61P 27/02 | (2006.01) | |
| G06T 7/00 | (2017.01) | |
| G06T 7/33 | (2017.01) | |

(52) U.S. Cl.
CPC ............ *A61K 38/07* (2013.01); *A61K 9/0048* (2013.01); *A61K 38/06* (2013.01); *A61K 38/08* (2013.01); *A61K 45/06* (2013.01); *A61B 3/102* (2013.01); *A61B 3/1233* (2013.01); *A61B 3/1241* (2013.01); *A61K 38/05* (2013.01); *A61K 47/02* (2013.01); *A61K 2300/00* (2013.01); *A61P 27/02* (2018.01); *C07K 5/06078* (2013.01); *C07K 5/06156* (2013.01); *C07K 5/0812* (2013.01); *C07K 14/4703* (2013.01); *C07K 14/4711* (2013.01); *G06T 5/50* (2013.01); *G06T 7/0016* (2013.01); *G06T 7/337* (2017.01); *G06T 2207/10101* (2013.01); *G06T 2207/20224* (2013.01); *G06T 2207/30041* (2013.01)

(58) Field of Classification Search
CPC .............. A61K 38/00; A61K 47/48646; A61K 9/0048; A61K 47/48415; A61K 47/48538; G01N 33/6896; G01N 2333/4709; G01N 2800/2821; G01N 33/5058; C07K 14/4711; C07K 2317/76; C07K 16/00; C12N 5/0621

See application file for complete search history.

(56) References Cited

U.S. PATENT DOCUMENTS

| | | |
|---|---|---|
| 6,191,154 B1 | 2/2001 | Landreth et al. |
| 7,560,100 B2 | 7/2009 | Pinchasi et al. |
| 7,728,043 B2 | 6/2010 | Kim |
| 7,781,396 B2 | 8/2010 | Gazit |
| 8,012,929 B2 | 9/2011 | Gazit |
| 8,067,372 B2 | 11/2011 | Paris et al. |
| 9,717,772 B2 | 8/2017 | Russ |
| 10,525,097 B2 * | 1/2020 | Russ ..................... A61K 38/06 |
| 2005/0119187 A1 | 6/2005 | Hammer et al. |
| 2006/0166879 A1 | 1/2006 | Bhushan et al. |

(Continued)

FOREIGN PATENT DOCUMENTS

| | | |
|---|---|---|
| JP | 2007-537699 | 12/2007 |
| JP | 2010-535728 | 11/2010 |

(Continued)

OTHER PUBLICATIONS

Baumritter et al., ARVO Annual Meeting Abstract; published May 2007.*

(Continued)

*Primary Examiner* — Chang-Yu Wang
(74) *Attorney, Agent, or Firm* — Mark S. Cohen; Pearl Cohen Zedek Latzer Baratz LLP

(57) ABSTRACT

Methods for the prevention and treatment of ocular disorders, in particular glaucoma, through blocking the toxic effects of β-amyloid (Aβ) derivatives, and pharmaceutical compositions for effecting such prevention and treatment thereof.

10 Claims, No Drawings

Specification includes a Sequence Listing.

(56) References Cited

U.S. PATENT DOCUMENTS

| | | | |
|---|---|---|---|
| 2006/0148905 | A1 | 7/2006 | Kim |
| 2006/0234947 | A1 | 10/2006 | Gazit |
| 2007/0021345 | A1 | 1/2007 | Gazit |
| 2007/0149466 | A1 | 6/2007 | Milburn et al. |
| 2009/0156471 | A1 | 6/2009 | Gazit et al. |
| 2010/0022459 | A1 | 1/2010 | Gazit |
| 2010/0093648 | A1 | 4/2010 | Cruz |
| 2010/0105608 | A1 | 4/2010 | Gazit |
| 2010/0143444 | A1 | 6/2010 | Anantharamaiah |
| 2010/0168084 | A1 | 7/2010 | Huber et al. |
| 2010/0204137 | A1 | 8/2010 | Russ |
| 2011/0200531 | A1 | 8/2011 | Tan |

FOREIGN PATENT DOCUMENTS

| | | |
|---|---|---|
| WO | WO 00/47193 | 8/2000 |
| WO | WO 2004/058239 | 7/2004 |
| WO | WO 2004/073630 | 9/2004 |
| WO | WO 2005/000193 | 1/2005 |
| WO | WO 2006/040157 | 4/2006 |
| WO | WO 2007/042262 | 4/2007 |
| WO | WO 2007/070372 | 6/2007 |
| WO | WO 2007/083949 | 7/2007 |
| WO | WO 2007/101732 | 9/2007 |
| WO | WO 2007/109620 | 9/2007 |
| WO | WO 2008/148564 | 12/2008 |
| WO | WO 2009/024346 | 2/2009 |
| WO | WO 2012/055945 | 5/2012 |
| WO | WO 2012/066549 | 5/2012 |
| WO | WO 2013/189606 | 12/2013 |

OTHER PUBLICATIONS

Lukiw et al. ,ARVO Annual Meeting Abstract; published May 2007.*
Ding et al. Vis Res. 2008, 48: 339-345. published Jul. 2007.*
Communication Pursuant to Article 94(3) EPC dated Feb. 10, 2014 From the European Patent Office Re. Application No. 08785661.3.
International Preliminary Report on Patentability dated Feb. 24, 2014 From the International Bureau of WIPO Re. Application No. PCT/EP2008/006888.
International Search Report and the Written Opinion dated Apr. 2, 2009 From the International Search Authority Re Application No. PCT/EP2008/006888.
Notice of Decision from Post-Prosecution Pilot Program (P3) Conference dated Aug. 24, 2016 From the USPTO Re. U.S. Appl. No. 12/733,270.
Official Action dated Jun. 8, 2015 From the USPTO Re. U.S. Appl. No. 12/733,270.
Official Action dated Apr. 11, 2013 From the USPTO Re. U.S. Appl. No. 12/733,270.
Official Action dated May 19, 2016 From the USPTO Re. U.S. Appl. No. 12/733,270.
Official Action dated Aug. 21, 2015 From the USPTO Re. U.S. Appl. No. 12/733,270.
Official Action dated Jan. 28, 2014 From the USPTO Re. U.S. Appl. No. 12/733,270.
Official Action dated Jan. 28, 2015 From the USPTO Re. U.S. Appl. No. 12/733,270.
Restriction OA dated Feb. 3, 2012 From the USPTO Re U.S. Appl. No. 12/733,270.
Bowie et al. "Deciphering the Message in Protein Sequences: Tolerance to Amino Acid Substitutions", Science, New Series, 247 (4948): 1306-1310,Mar. 16, 1990.
Burgess et al. "Possible Dissociation of the Heparin-hinding and Mitogenic Activities of Heparin-binding (Acidic Fibroblast) Growth Facror-1 from Its Receptor-binding Activities by Site-directed Mutagenesis of a Single Lysine Residue", The Journal of Cell Biolo11:v,111: 2129-2138, Nov. 1990.
Chapple et al, "Unfolding Retinal Dystrophies: A role for Molecular Chaperones?" Trends in Molecular Medicine 7(9): 414-421, Sep. 2001.
Jia et al. "Effect of General Anesthetics on IOP in Rats with Experimental Aqueous Outflow Obstruction", Investigative Ophtha!niO!ogy & Visual Science 41(11), Oct. 2000.
Levin "Neuroprotection and Neuroregeneration", In Glaucoma. Elsevier, London: 579-589, 2009.
Libby et al. "Susceptibility to Neurodegeneration in a Glaucoma is Modified by Bax Gene Dosage", PLOS Genetics, 1(1)e4: 17-26, 2005.
McKinnon "Glaucoma: Ocular Alzheimeer's Disease?", Frontiers in Bioscience 8: 1140-1156, Sep. 1, 2003.
National Eye institute "Facts About Glaucoma" The National institute of Health, USA, p. 1-10, May 31, 2015.
Pawson et al. "Assembly of Cell Regulatory Systems Through Protein Interaction Domains", Science 300: 445-452, Apr. 18, 2003.
Seullica et al. "Diagnosis and Classification of Macular Degenerations: An Approach Based on Retinal Function Testing", Documenta Ophthalmologica 102: 237-250, 2001.
The fact of the aromatic amino acids retrieved from the website: www.russelllab.org/aas/aromatic.html on Dec. 18, 2017.
"Facts About Glaucoma" National Eye Health Education Program; Downloaded from the Internet at: www.nei.gov/glaucoma on Oct. 18, 2018.
Jia et al. "Potential therapeutic strategies for Alzheimer's disease targeting or beyond β-amyloid: insights from clinical trials" Hindawi Publishing Corporation, BioMed research international. 2014;2014:22 pp.
Weinreb et al. "Oral memantine for the treatment of glaucoma: design and results of 2 randomized, placebo-controlled, phase 3 studies" Ophthalmology. Dec. 1, 2018;125(12):1874-85.
About Glaucoma Facts sheets retrieved from the National Eye Institute website: www.nei.nih.gov/health/glaucoma/glaucoma_facts on May 31, 2015.
Liubl et al; Drusen deposits associated with aging and age-related macular degeneration contain nonfibriliar amyloid oligomers. J. Clin. Invest. 2006; 116:378-385.
Steuer et al; Functional Characterization and Comparison of the Outer Blood-Retina Barrier and the Blood-Brain Barrier Invest., Ophthatmol. Vis.Sci 2005; 46:1047-1053.
Hall, Secondary Glaucoma; Clin. Exp. Optom. 2000; 83:3:190-194.
Ding et al. Targeting Age-related Macular Degeneration with Alzheimer's Disease Based Immunotherapies; Anti-Amyloid-β Antibody Atenuates Pathologies in an Age-related Macular Degeneration Mouse Model Vis. Res. 2008; 48:339-345.
Johnson et al. The Alzheimer's Aβ-peptide is deposited at sits of complement activation in pathologic deposits associated with aging and age-related macular degeneration; PNAS; 2002; 99:11830-11835.
Lightman et al; Assessment of the Permeability of the Blood-Retinal Barrier in Hypertensiv Rats. Hypertension.. 1987; 10:390-395.
Yoshida et al; The potential role of amyloid β in the pathogenesis of age-related macular degeneration: J. Clin. Invest. 2005; 115:2793-2800.
Bayer et al; Association of Glaucoma with Neurodegenerative Diseases with Apoptotic Cell Death: Alzheimer's Disease and Parkinson's Disease. Am. J. Ophthamol. 2002; 133:135-137.
Kaarairanta et al; Age Related Macular Degeneration (AMD): Alzheimer's Disease in the Eye? J. Alzheimer's disease 2011; 24; 615-631.
Leger et al; Protein Aggregation in the Aging Retina. J. Neuropathol. Exp. Neurol. 2011; 70:63-68.
Wang et al; Altered Function of Factor I Caused by Amyloid β: Implication for Pathogenesis of Age-Related Macular Degeneration from Drusen; J. Immunol. 2008; 181:712-720.
Rovner et al. Alzheimer's & Dementia; 2009; 5:12-17.
Sivak, The aging eye: Common Degenerative Mechanisms between the Alzheimer's Brain and Retinal Disease: IOVS, 2013; 54:871-880.
Wostyn et al. Alzheimer's disease and glaucoma: is there a causal relationship? The British J. Opthalmol. Apr. 2009, DOI:10.1136/bjo.2008.148064.

(56) References Cited

OTHER PUBLICATIONS

Bayer et al. High Occurrence Rate of Glaucoma among Patients with Alzheimer's Disease. Eur. Neurol. 2002; 47:165-168.
Ohno-Matsui, Prog. in Retinal and Eye Res. 2011; 30:217-238.
Rosenfeld et al., Retinal Physician, published Nov. 1, 2009, retrieved from the website: www/retinalphysician.com/issues/2009/nov-dec/preclinical-and-phase-1-drugs-in-development-for-dry-AMD-an-overview.
Chiu et al., Chapter 8: Progressive Neurodegeneration of Retina in Alzheimer's disease—Are beta-amyloid peptide and Tau New pathological factors in Glaucoma? 2013 Glaucoma—Basic and Clinical Aspects, retrieved from http://dx.doi.org/10.5772/53428 on Jul. 30, 2019, pp. 157-177.
Notice of Reason for Rejection dated Feb. 28, 2017 From the Japan Patent Office Re. Application No. 2015-517634. (4 Pages).
Translation of Notice of Reason for Rejection dated Feb. 28, 2017 From the Japan Patent Office Re. Application No. 2015-517634. (9 Pages).
Frydman-Marom et al. "The General Amyloid Formation Inhibition Effect of a Designed Small Aromatic Beta-BreakingPeptide", Amyloid, 18(3): 119-127, Sep. 2011.
Sun et al. "A Survey of Peptides With Effective Therapeutic Potential in Alzheimer's Disease Rodent Models or in Human Clinical Studies", Mini-Re,ie,vs in Medicinal Chemistry, 12(5): 388-398, May 2012.
International Preliminary Report on Patentability dated Dec. 31, 2014 From the International Bureau of WIPO Re. Application No. PCT/EP2013/001832.
International Search Report and the Written Opinion dated May 15, 2014 from the International Searching Authority Re. Application No. PCT/EP2013/001832.
Fradinger et al. "C-Terminal Peptides Coassemble Into A[Beta]42 Oligomers and Protect Neurons Against A[Beta]42-INduced Neurotoxicity", Proc. Natl. Acad. Sci. USA, PNAS, XP002723831, 105(37: 14175-14180, Sep. 16, 2008.
Frydman-Marom et al. "Cognitive-Performance Recovery of Alzheimer's Disease Model Mice by Modulation of Early Soluble Amyloidal Assemblies", Angewandte Chemie, International Edition, XP002601658, 48(11): 1981-1986, 01 Jan. 1, 2009 p. 2016 1-h col., Para 2.
Guo et al. "Targeting Amyloid-Beta in Glaucoma Treatment", Proc. Natl. Acad. Sci. USA, PNAS, XP002471873, 104(33): 13444-13449, Aug. 14, 2007.
Ladiwala et al. "Aromatic Small Molecules Remodel Toxic Soluble Oligomers of Amyloid Beta Through Three Independent Pathways", The Journal of Biological Chemistry, XP002723828, 286(5): 3209-3218, Feb. 4, 2011.
Luna et al. "Resveratrol Prevents the Expression of Glaucoma Markers Induced by Chronic Oxidative Stress in Trabecular Meshwork Cells", Food and Chemical Toxicology, XP025769233, 47(1): 198-204, Jan. 1, 2009.
McLaurin et al. "Inositol Stereoisomers Stabilize an Oligomeric Aggregate of Alzheimer Amyloid Beta Peptide and Inhibit A[Beta]-Induced Toxicity", the Journal of Biological Chemistry, XP003010970, 275(24): 18495-18502, Jun. 16, 2000.
Rigacci et al. "A[Beta](1-42) Aggregates Into Non-Toxic Amyloid Assemblies in the Presence of the Natural Polyphenol Oleuropein Aglycon", Current Alzheimer Research, XP009177758, 8(8): 841-852, Dec. 2011.
Sheu et al. "Resveratrol Protects Human Retinal Pigment Epithelial Cells From Acrolein-Induced Damage", Journal of Ocular Pharmacology and Therapeutics, Xl:'002723830, 26(3):231-236, Jun. 2010.
Ladiwala et al. "Ressveratrol Selectively Remodels Soluble Oligomers and Fibrils of Amyloid A[Beta] Into Off-Pathway Conformers" the journal of Biological Chemistry, XP002723829, 285 (31): 24228-24237, Jul. 30, 2010.
Yun et al "Paradoxical Strategy for Treating Chronic Diseases Where the Therapeutic Effect Is Derived From Compensatory Response Rather Than Drug Effect" Medical Hypotheses, XP004952012, 64(5): 1050-1059, Jan. 1, 2005, p. 1052, 1-h col., Lines 24-27, p. 1053, r-h col., Lines 3-12.
Zhang et al., "Epigallocatcchin Gallate, An Active Ingrediant From Green Tea, Attenuates Damaging Influences to the Retina Caused by Ischemia /Reperfusion" Brain Research, XP022156863, 1159: 40-53, Available Online May 26, 2007.

\* cited by examiner

METHODS FOR THE TREATMENT OF GLAUCOMA AND AGE-RELATED MACULAR DEGENERATION BY A PEPTIDE D-TRP-AIB

CROSS REFERENCE TO RELATED APPLICATIONS

This application is a Continuation application of U.S. Pat. No. 10,525,097 filed Nov. 17, 2016, which is a Continuation of U.S. patent application Ser. No. 12/733,270 filed on Apr. 2, 2010 and now abandoned, which is a National Phase of PCT International Patent Application No. PCT/EP2008/006888 having International Filing Date of Aug. 21, 2008, which claims the benefit of priority under 35 USC § 119(e) of Paris Patent Application No. 07253904.2 filed on Oct. 2, 2007, and of U.S. Provisional Patent Application No. 60/965,650 filed on Aug. 21, 2007. The contents of the above listed applications are all incorporated by reference as if fully set forth herein in their entirety.

SEQUENCE LISTING STATEMENT

The ASCII file, entitled 68149 SequenceListing.txt, created on Nov. 17, 2016, comprising 8,673 bytes, submitted concurrently with the filing of this application is incorporated herein by reference.

FIELD OF INVENTION

The present invention is concerned with methods for the prevention and treatment of ocular disorders, in particular glaucoma, through blocking the toxic effects of β-amyloid (Aβ) derivatives, and pharmaceutical compositions for effecting such prevention and treatment thereof.

BACKGROUND

Studies have shown that glaucoma is the second leading cause of blindness in the United States [Leske M C. The epidemiology of open-angle glaucoma: a review. Am J Epidemiology 1983; 118: 166-191]. The pathologic correlate of glaucoma is the progressive degeneration of retinal ganglion cells and their axons which form the optic nerve.

The classification of glaucoma includes the following different types: Primary angle-closure glaucoma, secondary open-angle glaucoma, steroid-induced glaucoma, traumatic glaucoma, pigmentary dispersion syndrome, pseudoexfoliation syndrome, secondary angle-closure glaucoma, neovascular glaucoma, uveitis and glaucoma and other non further specified eye pathologies. In addition, age-related macular degeneration is a condition which reflects features of glaucoma and leads to a progressive loss of vision, leading finally to blindness.

In the past, the definition of glaucoma included an elevation in the intraocular pressure (IOP) over a normal range. However, many individuals with clearly elevated IOP do not develop glaucoma, and up to 50% of patients with glaucoma do not have an increased IOP.

Currently available medications for the treatment of glaucoma belong to several pharmacological classes, including β-adrenergic blockers, cholinergic agonists, carbonic anhydrase inhibitors, alpha agonists. All operate under a mechanism whereby the IOP is lowered. These existing therapies are typically administered as eye drops. Hyperosmotics may be administered intravenously for emergency treatment. In addition, laser therapy and surgical approaches are applied in special cases.

Irrespective of therapy, after 20 years of follow-up in glaucoma patients, glaucoma-related blindness will have reached 27% in at least one eye and 9% in both eyes [Hattenhauer M G, Johnson D H, Ing H H, et al. The probability of blindness from open-angle glaucoma. Ophthalmology 1998; 105: 2099-2104]. Thus, there exists a significant unmet medical need for alternative treatment strategies. Particularly for patients with progressive glaucomatous damage under normalized IOP, a therapy focusing on the rescue of degenerating retinal ganglion cells is needed.

There are different theories regarding the cause for the degeneration of the retinal ganglion cells including mechanical, vascular and excitotoxic mechanisms. Only recently, β-amyloid (Aβ) has been found to co-localize with dying retinal ganglion cells [McKinnon S J. Glaucoma: Ocular Alzheimer's disease? Front Biosci. 2003; 8: 1140-1156; Yoneda S, Hara H, Hirata A, Fukushima M, Inomata Y, Tanihara H. Vitreous fluid levels of beta-amyloid ((1-42)) and tau in patients with retinal diseases. Jpn J Ophthalmol. 2005; 49(2): 106-108]. Animal studies demonstrate that, particularly, the soluble $A\beta_{1-42}$ peptide oligomers are very potent toxins for retinal ganglion cells [Dahlgren K N, Manelli A M, Stine W B Jr, Baker L K, Krafft G A, LaDu M J. Oligomeric and fibrillar species of amyloid-beta peptides differentially affect neuronal viability. J Biol Chem. 2002; 277(35): 32046-32053uo L, Salt T E, Luong V, Wood N, Cheung W, Maass A, Ferrari G, Russo-Marie F, Sillito A M, Cheetham M E, Moss S E, Fitzke F W, Cordeiro F. Targeting amyloid-β in glaucoma treatment. PNAS 2007; 104 (33): 13444-13449].

The recently published study of Guo, et al. (2007) demonstrated that inhibition of Aβ aggregation reduces glaucomatous degeneration of retinal ganglion cells. The inhibitors used in these animal experiments were Congo red and Aβ antibodies. These agents are pharmacological research tools only and are not appropriate for treatment of humans for various reasons.

Congo red (sodium salt of benzidinediazo-bis-1-naphtylamine-4-sulfonic acid) is a diazo dye. Its original use in the textile industries has long been abandoned because of its toxicity. Congo red binds with moderate specificity to amyloid fibres and is used for histopathological staining. Due to its toxicity, the substance cannot be administered systemically in humans. For the animal experiments, the dye was injected directly into the eyes. The intense color of the solution is, besides the burden of the procedure, prohibitive for an intraocular route of application in humans. As a consequence, Congo red preparations cannot be provided as medication for treatment of glaucoma in humans.

Aβ antibodies are known to block Aβ aggregation relatively specifically [Bard F, Cannon C, Barbour R, Burke R L, Games D, Grajeda H, Guido T, Hu K, Huang J, Johnson-Wood K, Khan K, Kholodenko D, Lee M, Lieberburg I, Motter R, Nguyen M, Soriano F, Vasquez N, Weiss K, Welch B, Seubert P, Schenk D, Yednock T. Peripherally administered antibodies against amyloid beta-peptide enter the central nervous system and reduce pathology in a mouse model of Alzheimer's disease. Nat Med. 2000; 6(8): 916-919]. However, the usefulness of anti-Aβ antibodies for the treatment of glaucoma in humans is limited by the known side effect of these biologicals to induce neutralizing antibodies which leads to a loss of efficacy after repeated administrations. Additional side effects are the provocation of immunogenic inflammatory reactions and the occurrence of antibody-induced microhemorrhages in the target organ [Vasilevko V, Cribbs D H. Novel approaches for immunotherapeutic intervention in Alzheimer's disease. Neurochem Int. 2006; 49(2): 113-126]. Moreover, antibodies are not orally available, which calls for (repeated) injections (frequently leading to skin irritations). Finally, antibody production at an industrial level is rather complicated and expensive.

Theoretically, β-secretase inhibitors could also have beneficial effects on Aβ-related neurotoxicity. However, the observed effects in rat retinal ganglion cells were not significant and this approach does not seem promising for further development in glaucoma [Guo et al. 2007].

It would be an advantage to provide novel methods for the prevention and treatment of ocular disorders, in particular glaucoma, and pharmaceutical compositions for effecting such prevention and treatment thereof. Additional needs in the art which are addressed by the invention will become apparent hereinafter, and still further needs will be apparent to one skilled in the art.

SUMMARY

What we therefore believe to be comprised by our invention may be summarized inter alia in the following words:

A method-of-treating a living animal, including a human, for the prevention and treatment of an optical condition associated with β-amyloid (Aβ) toxicity, comprising the step of administering to the living animal a therapeutically effective amount of a peptide comprising amino acid sequence X-Y or Y-X, wherein X is an aromatic amino acid and Y is one or more additional amino acid other than glycine, the peptide having at least 2 amino acid residues and less than 15 amino acid residues, thereby inhibiting Aβ formation and/or occurrence of said Aβ, which is effective for alleviation of the condition.

Such a method wherein the condition is selected from the group consisting of primary angle-closure glaucoma, secondary open-angle glaucoma, wide-angle glaucoma, steroid-induced glaucoma, traumatic glaucoma, pigmentary dispersion syndrome, pseudo exfoliation syndrome, secondary angle-closure glaucoma, neovascular glaucoma, uveitis and glaucoma, age-related macular degeneration, diabetic retinopathy, degenerative optic neuropathy and eye pathologies characterized by a progressive loss of vision leading finally to blindness.

Such a method comprising the step of co-administering to the living animal a therapeutically effective amount of a peptide as described above in combination with at least one additional pharmaceutical agent which is effective in treating the optical condition, wherein the combination of the peptide and the at least one additional pharmaceutical agent is effective in treating the condition.

Such a method wherein the at least one additional pharmaceutical agent is selected from medications administered to treat eye diseases containing anti-glaucoma drugs, antibiotics, anti-inflammatory drugs, steroids, anti-allergic drugs and artificial tear fluid.

Such a method wherein the at least one additional pharmaceutical agent is selected from acetazolamide, diclofenamide, carteolol, timolol, metipranolol, betaxolol, pindolol, levobunolol, brimonidine, clonidine, pilocarpine, carbachol, dipivefrine, apraclonidine, brinzolatnide, dorzolamide, bimatoprost, travaprost, latanoprost, chlortetracycline, ciprofloxacine, ofloxacine, fusidinic acid, gentamicine, kanamycin, levofloxacine, lomefloxacine, oxytetracycline, natamycine, azidamfenicole, chloramphenicole, tobramycine, erythromycine, polymyxin-B, acaclovir, trifluridine, betamethasone, dexamethasone, fluorometholone, hydrocortisone, prednisolone, rimexolone, cromoglicate, azelastine, lodoxamide, emedastine, nedocromile, levocabastine, olopatadinea, ketotifene, hypromellose, carbomere, hyaluronate, carmellose, hypromellose, povidone, hyetellose, polivinylalcohole, dexpanthenole, tetryzoline, troxerutine, tramazoline, naphazoline, xylometazoline, phenylephrine and antazoline.

Such a method wherein the peptide is administered once a day, twice a day or three times a day.

Such a method wherein the peptide is administered chronically.

Such a method wherein the peptide is administered in the form of eye drops, eye creams, and intraocular depot formulations.

Such a method wherein the peptide is administered in an immediate or modified release formulation.

Such a method wherein the peptide and the at least one additional pharmaceutical agent are administered conjointly.

Such a method wherein the peptide and the at least one additional pharmaceutical agent are administered in a single formulation.

A further aspect of the invention relates to a pharmaceutical composition comprising a peptide as described above, or a pharmaceutically acceptable addition salt thereof, alone or in combination with one or more pharmaceutically acceptable carrier and/or excipient.

Such a pharmaceutical composition further comprising at least one additional pharmaceutical agent which is effective in treating the optical condition, wherein the combination of the peptide and the at least one additional pharmaceutical agent is effective in treating the condition, or a pharmaceutically acceptable addition salt thereof, alone or in combination with one or more pharmaceutically acceptable carrier and/or excipient.

A further aspect of the invention relates to the use of peptide comprising amino acid sequence X-Y or Y-X, wherein X is an aromatic amino acid and Y is one or more additional amino acid other than glycine, the peptide having at least 2 amino acid residues and less than 15 amino acid residues, for the manufacture of a medicament for the prevention and treatment of an optical condition associated with β-amyloid (Aβ) toxicity.

Such a use characterized in that the condition is selected from the group consisting of primary angle-closure glaucoma, secondary open-angle glaucoma, wide-angle glaucoma, steroid-induced glaucoma, traumatic glaucoma, pigmentary dispersion syndrome, pseudo exfoliation syndrome, secondary angle-closure glaucoma, neovascular glaucoma, uveitis and glaucoma, age-related macular degeneration, diabetic retinopathy, degenerative optic neuropathy and eye pathologies characterized by a progressive loss of vision leading finally to blindness.

Such a use characterized in that the medicament comprises the above-identified peptide in combination with at least one additional pharmaceutical agent which is effective in treating such optical conditions, further characterized in that the additional pharmaceutical agent is selected from anti-glaucoma drugs, antibiotics, anti-inflammatory drugs, steroids, anti-allergic drugs and artificial tear fluid.

DETAILED DESCRIPTION

The present invention addresses the limitations of conventional therapy for optical disorders and provides for a pharmaceutically acceptable therapy to effectively treat the loss of eyesight in humans with glaucoma and other degenerative ocular disorders. The underlying mechanism is a prevention or reversal of the loss of retinal ganglion cells through blocking the toxic effects of Aβ species.

Representative substances described for the instant therapy were initially designed for the treatment of diseases characterized by formation of amyloid fibrils, such as type II diabetes and prion diseases [Porat Y, Mazor Y, Efrat S, Gazit E. Inhibition of islet amyloid polypeptide fibril formation: A potential role for heteroaromatic interactions. Biochemistry 2004; 43:14454-14462], and degenerative diseases of the brain including Alzheimer's dementia [GAZIT, E., US Published Application No. US2006/0234947 A1]. More specifically, Gazit discloses that short chain peptides, possibly comprising modified amino acids such as aminoisobutyric acid, have application in the disruption of the formation of toxic Aβ species by interacting with molecular recognition processes and amyloid fibril self-assembly. [Gazit, 2006] With the instant invention, we have determined that these substances show therapeutic effects in another organ system distinct from the brain, i.e., the eyes. The substances described for use according to the invention demonstrate therapeutic effect in the prevention and treatment of retinal ganglion cell loss in animal models of glaucoma. Compared to known agents, Congo red and Aβ antibodies, the substances of the instant invention have the following advantages:

They are small molecules which can be produced cost-effectively in large scale.

They can easily be administered to patients, either orally (for instance as tablets or capsules), or locally (for instance eye drops, eye cream, intraocular depot).

Injections are not necessary.

They are well tolerated even under continuous long-term application.

They have simple pharmacokinetic properties allowing a 1-3 times daily intake regimen.

They show a high affinity and specificity to Aβ species in the retina.

They may have a dual mechanism of action, i.e. they act as β-sheet breakers and oligomerisation inhibitors resulting in a pronounced therapeutic efficacy. They can be combined with other treatments, such as any of the IOP-lowering glaucoma drugs used hitherto and also with other potentially Aβ-directed and protective treatments.

Methods comprising the administration of these substances find application in treating patients with all types of ocular disorders including all forms of glaucoma, as aforementioned, and pigmentary dispersion syndrome, pseudoexfoliation syndrome, secondary angle-closure glaucoma, neovascular glaucoma, uveitis, age-related macular degeneration, diabetic retinopthia, degenerative optic neuropathy and other eye pathologies characterized by a progressive loss of vision leading finally to blindness known to those skilled in the art. Such conditions have in common a progressive decline of eyesight related to a degenerative process of retina or optic nerve. Treatment is possible at all stages of disease progression including very early stages as a prophylactic. The clinical effects may patients already suffering from a glaucomatous degeneration, and second a slowing-down or stopping of the progressive worsening of the eyesight. Even patients who experience blindness in one or two eyes related to glaucoma may regain eyesight to some extent.

The instant methods optionally comprise administering preparations containing these substances on a continuous basis to provide best treatment outcomes. Depending on the type and the stage of the underlying disease treatment, cycles of some days to several months are possible. Under certain conditions also continuous long-term treatment is possible.

The instant methods optionally comprise administering at least one additional pharmaceutical agent which is known in the art to be effective in the treatment of ocular disorders. These additional agents may be selected from the general class of anti-glaucoma drugs including those mentioned above, antibiotics virostatics, steroids, anti-allergic drugs, artificial tears and other drugs used for local and systemic eye treatment. Representative anti-glaucoma drugs include acetazolamide, diclofenamide, carteolol, timolol, metipranolol, betaxolol, pindolol, levobunolol, brimonidine, clonidine, pilocarpine, carbachol, dipivefrine, apraclonidine, brinzolamide, dorzolaminde, bimatoprost, travaprost, and latanoprost. Representative antibiotics used for eye infections are chlortetracycline, ciprofloxacine, ofloxacine, fusidinic acid, gentamicine, kanamycine, levofloxacine, lomefloxacine, oxytetracycline, natamycine, azidamfenicole, chloramphenicole, tobramycine, erythromycine, and polymyxin-B. Representative virostatics include acaclovir, and trial uridine. Representative steroids include betamethasone, dexamethasone, fluorometholone, hydrocortisonebe twofold, first an acute improvement in eyesight in those, prednisolone, and rimexolone. Representative anti-allergic drugs include cromoglicate, azelastine, lodoxamide, emedastine, nedocromile, levocabastine, olopatadinea and ketotifen. Representative artificial tears include hypromellose, carbomere, hyaluronate, carmellose, hypromellose, povidone, hyetellose, polivinylalcohole, and dexpanthenole. Other representative commonly used eye therapeutics are tetryzoline, troxerutine, tramazoline, naphazoline, xylometazoline, phenylephrine, antazoline.

The following peptides as described in US Published Application No. US2006/0234947 A1 are representative of those substances which are active in the methods of the present invention. D-Phe-D-Phe-D-Pro (SEQ ID NO. 1), Aib-D-Phe-D-Asn-Aib (SEQ ID NO. 2), D-Phe-D-Asn-D-Pro (SEQ ID NO. 3), Aib-Asn-Phe-Aib (SEQ ID NO. 4), Gln-Lys-Leu-Val-Phe-Phe (SEQ ID NO. 5), Tyr-Tyr (SEQ ID NO. 6), D-Phe-D-Phe-D-Pro (SEQ ID NO. 7), Aib-D-Phe-D-Asn-Aib (SEQ ID NO. 8), Aib-Asn-Phe-Aib (SEQ ID NO. 9), Tyr-Tyr (SEQ ID NO. 10), Tyr-Tyr-NH$_2$ (SEQ ID NO. 11), Aib-Phe-Phe (SEQ ID NO. 12), Asn-Tyr-Aib (SEQ ID NO. 13), Asn-Tyr-Pro (SEQ ID NO. 14), β-aminoisobutyric acid (Aib)-D-Pro-D-Tyr-D-Asn (SEQ ID NO. 15), D-Tyr-Aib (SEQ ID NO. 16), D-Pro-D-Tyr (SEQ ID NO. 17). D-Tyr-D-Pro (SEQ ID NO. 18), Asn-Tyr-Tyr-Pro (SEQ ID NO. 19), Tyr-Tyr-Aib (SEQ ID NO. 20), Aib-Tyr-Tyr (SEQ ID NO. 21), Aib-Tyr-Tyr-Aib (SEQ ID No. 22), D-Asn-Tyr-Tyr-D-Pro (SEQ ID NO. 23), Pro-Tyr-Tyr (SEQ ID NO. 24), Tyr-Tyr-Pro (SEQ ID NO. 25), Pro-Tyr-Tyr-Pro (SEQ ID NO. 26), D-Tyr-D-Tyr (SEQ ID NO. 27), D-Pro-Aib (SEQ ID NO. 28), D-Phe-D-Pro (SEQ ID NO. 29), D-Trp-Aib (SEQ ID NO. 30), D-Trp-D-Pro (SEQ ID NO. 31), D-Phe-Pro (SEQ ID NO. 32), and Pro-D-Phe (SEQ ID NO. 33). Unless otherwise noted, the residue Aib is understood to mean a aminoisobutyric acid.

It will be apparent to those skilled in the art that the described substances are merely representative in nature and that alternative substances are known to one of ordinary skill in pharmacology.

The term "analog" or "derivative" is used herein in the conventional pharmaceutical sense, to refer to a molecule that structurally resembles an active substance of the instant method (such as D-Trp-Aib), but has been modified in a targeted and controlled manner to replace one or more specific substituents of the referent molecule with an alternate substituent, thereby generating a molecule which is structurally similar to the reference molecule. Synthesis and screening of analogs (e.g., using structural and/or biochemical analysis), to identify slightly modified versions of a known substance which may have improved or biased traits (such as higher potency and/or selectivity at a specific targeted receptor type, greater ability to penetrate mammalian blood-brain barriers, fewer side effects, etc.) is a drug design approach that is well known in pharmaceutical chemistry.

In addition, using methods known to those skilled in the art, analogs and derivatives of the substances of the invention can be created which have improved therapeutic efficacy in controlling β-amyloid (Aβ) toxicity, i.e., higher potency and/or selectivity at a specific targeted receptor type, either greater or lower ability to penetrate mammalian blood-brain barriers (e.g., either higher or lower blood-brain barrier permeation rate), fewer side effects, etc.

Due to their high degree of activity and their low toxicity, together presenting a most favorable therapeutic index, the substances of the invention may be administered to a subject, e.g., a living animal (including a human) body, in need thereof, for the treatment, alleviation, or amelioration, palliation, or elimination of an indication or condition which is susceptible thereto, or representatively of an indication or condition set forth elsewhere in this application, preferably concurrently, simultaneously, or together with one or more pharmaceutically-acceptable excipients, carriers, or diluents, especially and preferably in the form of a pharmaceutical composition thereof, whether by oral, rectal, or parental (including intravenous, intraocular, and subcutaneous) or in some cases even topical route (including eye drops, eye creams, and intraocular depot formulations), in an effective amount. Suitable dosage ranges include 1-1000 milligrams daily, alternately 10-500 milligrams daily, and optionally 50-500 milligrams daily, depending as usual upon the exact mode of administration, form in which administered, the indication toward which the administration is directed, the subject involved and the body weight of the subject involved, and the preference and experience of the physician or veterinarian in charge.

The term "therapeutically effective" applied to dose or amount refers to that quantity of a substance or pharmaceutical composition that is sufficient to result in a desired activity upon administration to a living animal body (including a human body) in need thereof. The term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). The term "pharmaceutically acceptable" may also mean approved by a regulatory agency of the Federal or a state government or listed in the U.S. Pharmacopeia or other generally recognized pharmacopeia for use in mammals, and more particularly in humans.

Substances of the present invention may be in the form of pharmaceutically acceptable salts. "Pharmaceutically acceptable salts" refers to those salts which possess the biological effectiveness and properties of the parent compound and which are not biologically or otherwise undesirable. The nature of the salt or isomer is not critical, provided that it is non-toxic and does not substantially interfere with the desired pharmacological activity.

The term "carrier" applied to pharmaceutical compositions of the invention refers to a diluent, excipient, or vehicle with which an active substance (such as D-Trp-Aib) is administered. Such pharmaceutical carriers may be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described in "Remington's Pharmaceutical Sciences" by A. R. Gennaro, $20^{th}$ Edition.

The term "about" or "approximately" usually means within 20%, alternatively within 10%, including within 5% of a given value or range. Alternatively, especially in biological systems, the term "about" means within about a log (i.e., an order of magnitude), including within a factor of two of a given value.

In conjunction with the methods of the present invention, also provided are pharmaceutical compositions comprising a therapeutically effective amount of the active substance. The compositions of the invention may further comprise a carrier or excipient (all pharmaceutically acceptable). The compositions may be formulated for once-a-day administration, twice-a-day administration, or three times a day administration. In addition, depot formulations are possible for implantation into the eye allowing application intervals of 3-12 months.

According to the present invention, the dosage form of the active substance may be a solid, semisolid, or liquid formulation according to the following.

The active substance of the instant invention may be administered orally, topically, parenterally, or mucosally (e.g., buccally, by inhalation, or rectally) in dosage unit formulations containing conventional non-toxic pharmaceutically acceptable carriers. In another embodiment for administration to pediatric subjects, the active substance may be formulated as a flavored liquid (e.g., peppermint flavor). The active substance may be administered orally in the form of a capsule, a tablet, or the like, or as a semi-solid, or liquid formulation (see Remington's Pharmaceutical Sciences, $20^{th}$ Edition, by A. R. Gennaro).

For oral administration in the form of a tablet or capsule, the active substance may be combined with non-toxic, pharmaceutically acceptable excipients such as binding agents (e.g., pregelatinized maize starch, polyvinylpyrrolidone or hydroxypropyl methylcelluose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like.

The tablets may be coated with a concentrated sugar solution which may contain e.g., gum arabic, gelatine, talcum, titanium dioxide, and the like. Alternatively, the tablets may be coated with a polymer that dissolves in a readily volatile organic solvent or mixture of organic solvents. In specific embodiments, the active substance is formulated into immediate-release (IR) or modified-release (MR) tablets. Immediate release solid dosage forms permit the release of most or all of the active ingredient over a short period of time, such as 60 minutes or less, and make rapid absorption of the drug possible. Modified release solid oral dosage forms permit the sustained release of the active substance over an extended period of time in an effort to maintain therapeutically effective plasma levels over similarly extended time intervals and/or to modify other pharmacokinetic properties of the active substance.

For the formulation of soft gelatin capsules, the active substances may be admixed with e.g., a vegetable oil or poly-ethylene glycol. Hard gelatin capsules may contain granules of the active substances using either the above mentioned excipients for tablets e.g., lactose, saccharose, sorbitol, mannitol, starches (e.g., potato starch, corn starch or amylopectin), cellulose derivatives or gelatine. Also liquids or semisolids of the drug may be filled into hard gelatine capsules.

The compositions of the invention may also be introduced in microspheres or microcapsules, e.g., fabricated from polyglycolic acid/lactic acid (PGLA) (see, e.g., U.S. Pat. Nos. 5,814,344; 5,100,669 and 4,849,222; PCT Publications No. WO 95/11010 and WO 93/07861). Biocompatible polymers may be used in achieving controlled release of an active substance, include for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

Formulation of an active substance in a semi-solid or liquid form may also be used. The substance may constitute between 0.1 and 99% by weight of the formulation, more specifically between 0.5 and 20% by weight for formulations intended for injection and between 0.2 and 50% by weight for formulations suitable for oral administration.

In one embodiment of the invention, the active substance is administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacologic action after administration, and to reduce variability in the plasma concentration of a drug throughout the dosage interval, thereby eliminating or reducing sharp peaks.

A modified release dosage form may comprise a core either coated with or containing an active substance. The core being is then coated with a release modifying polymer within which the active substance is dispersed. The release modifying polymer disintegrates gradually, releasing the active substance over time. Thus, the outer-most layer of the composition effectively slows down and thereby regulates the diffusion of the active substance across the coating layer when the composition is exposed to an aqueous environment, i.e. the gastrointestinal tract. The net rate of diffusion of the active substance is mainly dependent on the ability of the gastric fluid to penetrate the coating layer or matrix and on the solubility of the active substance itself.

In another embodiment of the invention, the active substance is formulated in an oral, liquid formulation. Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound.

For oral administration in liquid form, the active substance may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (BHA, BHT, propyl gallate, sodium ascorbate, citric acid) may also be added to stabilize the dosage forms. For example, solutions may contain from about 0.2% to about 20% by weight of the active substance, with the balance being sugar and mixture of ethanol, water, glycerol and propylene glycol. Optionally, such liquid formulations may contain coloring agents, flavoring agents, saccharine and carboxymethyl-cellulose as a thickening agent or other excipients.

In another embodiment, a therapeutically effective amount of the active substance is administered in an oral solution containing a preservative, a sweetener, a solubilizer, and a solvent. The oral solution may include one or more buffers, flavorings, or additional excipients. In a further embodiment, a peppermint or other flavoring is added to the active substance oral liquid formulation.

For administration by inhalation, the active substance may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Solutions for parenteral applications by injection may be prepared in an aqueous solution of a water-soluble pharmaceutically acceptable salt of the active substances, preferably in a concentration of from about 0.5% to about 10% by weight. These solutions may also contain stabilizing agents and/or buffering agents and may conveniently be provided in various dosage unit ampoules.

The formulations of the invention may be delivered parenterally, i.e., by intraocular, intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. Alternatively, the active ingredient may be in powder form for reconstitution with a suitable vehicle, e.g., sterile pyrogen-free water, before use.

The invention also provides a pharmaceutical pack or kit comprising one or more containers containing the active substance and, optionally, more of the ingredients of the formulation. In a specific embodiment, the active substance is provided as an oral solution (for example 2 mg/ml) for administration with the use of a 2 teaspoon capacity syringe (DOSAGE KORC®). Each oral syringe has hatch marks for measurement, with lines on the right side of the syringe (tip down) representing tsp units, and those on the left representing ml units.

The optimal therapeutically effective amount may be determined experimentally, taking into consideration the exact mode of administration, from in which the drug is administered, the indication toward which the administration is directed, the subject involved (e.g., body weight, health, age, sex, etc.), and the preference and experience of the physician or veterinarian in charge.

Dosage units for rectal application may be solutions or suspensions or may be prepared in the form of suppositories or retention enemas comprising the substances of the invention in a mixture with a neutral fatty base, or gelatin rectal capsules comprising the active substances in admixture with vegetable oil or paraffin oil.

Toxicity and therapeutic efficacy of the compositions of the invention may be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and it may be expressed as the ratio LD50/ED50. Compositions that exhibit large therapeutic indices are preferred.

Suitable daily doses of the active substance of the invention in therapeutic treatment of humans are about 0.01-10 mg/kg bodyweight on peroral administration and 0.001-10 mg/kg bodyweight on parenteral administration.

Treatment duration may be short-term, e.g., several weeks (for example 8-14 weeks), or long-term until the attending physician deems further administration no longer is necessary.

The active substance of the instant invention may be administered as a monotherapy, or in combination with another substance prescribed for the treatment of an optical condition associated with β-amyloid (Aβ) toxicity or, more specifically, glaucoma.

The term "combination" applied to active substances is used herein to define a single pharmaceutical composition (formulation) comprising two active substances (e.g., a pharmaceutical composition comprising an active substance as described herein and another substance prescribed for the treatment of an optical condition associated with β-amyloid (Aβ) toxicity or, more specifically, glaucoma) or two separate pharmaceutical compositions, each comprising an active substance (e.g. a pharmaceutical composition comprising a an active substance of the instant invention or another substance prescribed for the treatment of an optical condition associated with β-amyloid (Aβ) toxicity or, more specifically, glaucoma), to be administered conjointly.

Within the meaning of the present invention, the term "conjoint administration" is used to refer to administration of an active substance as described herein and a second active substance (e.g. another substance prescribed for the treatment of an optical condition associated with β-amyloid (Aβ) toxicity or, more specifically, glaucoma) simultaneously in one composition, or simultaneously in different compositions, or sequentially. For the sequential administration to be considered "conjoint", however, an active substance as described herein and the second active substance must be administered separated by a time interval which still permits the resultant beneficial effect for treating an optical condition associated with β-amyloid (Aβ) toxicity in a mammal.

The Experimental substances of the instant invention may be useful for the treatment of glaucoma and also age- and/or Alzheimer's disease-related RGC dysfunction as the role of Aβ has also been suggested for the latter condition. Moreover, plausible synergistic therapeutic effects can be expected from a combined treatment with intraocular pressure lowering agents currently used in glaucoma as well as proposed future therapies such as antioxidants, calcium channel blockers, NO synthase inhibitors, neurotrophins and antiapoptotic.

The present invention provides novel, valuable, and surprising applications and uses for substances in the methods of the present invention, as well as novel pharmaceutical compositions thereof, possessed of at least one of the herein-described characteristics and/or advantages.

The method—of treating a living animal body with a substance of the invention, for the inhibition of progression or alleviation of the selected ailment therein, is as previously stated by any normally-accepted pharmaceutical route, employing the selected dosage which is effective in the alleviation of the particular ailment desired to be alleviated.

Use of the substances of the present invention in the manufacture of a medicament for the treatment of a living animal for inhibition of progression or alleviation of selected ailments or conditions, particularly ailments or conditions such as optical conditions associated with β-amyloid (Aβ) toxicity, is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active substance with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or topical use, also in accord with the foregoing.

Pharmacology—Summary

The method of using the active substance of the present invention, and pharmaceutical compositions thereof, are characterized by unique advantageous and unpredictable properties, rendering the "subject matter as a whole", as claimed herein, unobvious. The methods and pharmaceutical compositions therefore have exhibited, in standard accepted reliable test procedures, the following valuable properties and characteristics:

Methods

In experimental model of glaucoma, there is increased expression of amyloid precursor protein (APP) and likely related apoptosis in retinal ganglion cells (RGC) [McKinnon, S. J.; Lehman, D. M.; Kerrigan-Baumrind, L. A.; Merges, C. A.; Pease, M. E.; Kerrigan, D. F.; Ransom, N. L.; Tahzib, N. G.; Reitsamer, H. A.; Levkovitch-Verbin, H; Quigley, H. A., and Zack, D. J. Caspase activation and amyloid precursor protein cleavage in rat ocular hypertension. Invest Ophthalmol Vis Sci. 2002 April; 43(4):1077-87]. Furthermore, injection of $A\beta_{1-42}$ induces apoptosis in RGC. Interference with APP-Aβ pathway such as ocular application of antibody, inhibition of β-secretase activity or oligomerisation inhibition prevents, at least temporally RGC apoptosis in glaucoma resulting from increased ocular pressure (Guo, et al., 2007). Therefore, it is likely that substances of the instant invention, which exhibit a dual mechanism of action, i.e., β-sheet breaking activity and oligomerisation inhibition, should even more effective, in particular if given not only at the time of increased ocular pressure induction, but also afterwards.

Experimental Procedure

Thus, in the male Dark Aguti rat model, glaucoma is produced by injection of hypertonic saline into episcleral veins of one eye to induce increased ocular pressure (chronic ocular hypertension—OHT), while the opposite eye serves as a control [Morrison J. C., Moore C. G., Deppmeier L. M., Gold B. G., Meshul C. K., Johnson E. C. A rat model of chronic pressure-induced optic nerve damage. Exp Eye Res. 1997; 64(1): 85-96] In treatment groups (N=4-8 per group), various doses of substances of the instant invention are injected intravitreally (in 5 μvolume) at the time of glaucoma induction and in some groups the administration continues for following 7 days to see whether such extended treatment results in increased efficacy. The extent of RGC apoptosis at 3 weeks and 6 weeks after chronic ocular hypertension (OHT) induction is assessed in each animal by dynamic confocal scanning laser ophthalmoscopy and fluorescent-labeled Annexin V. Animals are sacrificed after 3 and 6 weeks and their eyes are enucleated and fixed in 4% paraformaldehyde overnight. Afterwards, retinas are separated for assessing apoptosis related changes, for example: as visualised with FITC Annexin V kit (BD Biosciences, Franklin Lakes, USA) [Cordeiro, M. F., Guo, L., Luong, V., Harding, G., Wang, W., Jones, H. E., Moss, S. E., Sillito, A. M., and Fitzke, F. W. 2004 Real-time imaging of single nerve cell apoptosis in retinal neurodegeneration. Proc Natl Acad Sci USA, 101, 13352-6; Kietselaer, B. L., Hofstra, L., Dumont, E. A., Reutelingsperger, C. P., and Heidendal, G. A. 2003 The role of labeled Annexin A5 in imaging of programmed cell death. From animal to clinical imaging. Q J Nucl Med, 47, 349-61], or TUNEL (dUTP nick end labeling) [Roche, In situ cell death detection kit, fluorescein labelled] [Szydlowska K., Kaminska B., Baude A., Parsons C. G., Danysz W. 2007 Neuroprotective activity of selective mGlu1 and mGlu5 antagonists in vitro and in vivo. Eur. J. Pharmacol. 554, 18-29.]. In animals treated with experimental substances of the instant invention, there is a decrease in RGC apoptosis at least at one time point assessed.

In a further experiment, rats are treated systemically (p.o. or i.p.) and the experiment is repeated as above. The aim of this study is to verify whether systemic administration produced sufficiently high concentrations in the eye. Therefore, additionally, concentrations of substances of the instant invention are analyzed in the vitreal space of the eye. In animals treated systemically with experimental substances, there is a decrease in RGC apoptosis at least at one time point assessed and significant concentrations of the experimental substances are detected in the vitreal space of the eye.

Additionally, effects of experimental substances on toxicity of RGC cells is verified in vitro. β-amyloid$_{1-42}$ is preaggregated for 7 days with an experimental substance (300, 100, 30, 10, 3, 1, 0.3 μM) or control and then part of this solution is added to primary RGC culture for 48 hours to produce a final concentration of 15 μM. During this incubation, cells stay in an incubator at 37° C., 95% humidity and 5% CO2. Afterwards, apoptosis/necrosis is verified using FITC Annexin V kit (BD Biosciences, Franklin Lakes, USA) [Vermes, I., Haanen, C., Steffens-Nakken, H., and Reutelingsperger, C. (1995) A novel assay for apoptosis. Flow cytometric detection of phosphatidylserine expression on early apoptotic cells using fluorescein labelled Annexin V. J Immunol Methods, 184, 39-51.] and optionally with propidium iodide [Szydlowska et al., 2007].

Statistical analysis is performed using One-Way ANOVA followed by post-hoc test (SigmaStat, Systat Software, Point Richmond, USA).

These data strongly suggest that experimental substances of the instant invention may be useful for the treatment of glaucoma and also age- and/or Alzheimer's disease-related RGC dysfunction as the role of Aβ has been suggested for the latter condition as well [Guo, et al., 2007; Parisi. V., Restuccia, R., Fattapposta, F., Mina, C., Bucci, M. G., and Pierelli, F. (2001) Morphological and functional retinal impairment in Alzheimer's disease patients. Clin Neurophysiol, 112, 1860-7; Iseri, P. K., Altinas, O., Tokay, T., and Yuksel, N. (2006) Relationship between cognitive impairment and retinal morphological and visual functional abnormalities in Alzheimer's disease. J Neuroophthalmol, 26, 18-24]. Moreover, plausible synergistic therapeutic effects can be expected from a combined treatment with intraocular pressure lowering agents currently used in glaucoma as well as proposed future therapies such as antioxidants, calcium channel blockers, NO synthase inhibitors, neurotrophins and antiapoptotic agents [Hartwick A. T. 2001. Beyond intraocular pressure: neuroprotective strategies for future glaucoma therapy. Optom Vis Sci 78, 85-94.].

CONCLUSIONS

In conclusion, from the foregoing, it is apparent that the present invention provides novel, valuable, and surprising applications and uses for substances in the methods of the present invention, as well as novel pharmaceutical compositions thereof, all possessed of the foregoing more specifically-enumerated characteristics and advantages.

The high order of activity of the described methods for using the active substances of the present invention and compositions thereof, as evidenced by the tests reported, is indicative of utility. Clinical evaluation in human beings has not been completed, however. It will be clearly understood that the distribution and marketing of any substance or composition falling within the scope of the present invention for use in human beings will of course have to be predicated upon prior approval by governmental agencies, such as the U.S. Federal Food and Drug Administration, which are responsible for and authorized to pass judgment on such questions.

The method—of treating a living animal body with a substance of the invention, for the inhibition of progression or alleviation of the selected ailment therein, is as previously stated by any normally-accepted pharmaceutical route, employing the selected dosage which is effective in the alleviation of the particular ailment desired to be alleviated.

Use of the substances of the present invention in the manufacture of a medicament for the treatment of a living animal for inhibition of progression or alleviation of selected ailments or conditions, particularly ailments or conditions such as optical conditions associated with β-amyloid (Aβ) toxicity, is carried out in the usual manner comprising the step of admixing an effective amount of a compound of the invention with a pharmaceutically-acceptable diluent, excipient, or carrier, and the method-of-treating, pharmaceutical compositions, and use of a compound of the present invention in the manufacture of a medicament.

Representative pharmaceutical compositions prepared by admixing the active substance with a suitable pharmaceutically-acceptable excipient, diluent, or carrier, include tablets, capsules, solutions for injection, liquid oral formulations, aerosol formulations, TDS formulations, and nanoparticle formulations, thus to produce medicaments for oral, injectable, or topical use, also in accord with the foregoing.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

What is claimed is:

1. A method of treating an optical condition associated with β-amyloid (Aβ) toxicity, said optical condition being glaucoma or age-related macular degeneration (AMD), the method comprising the step of administering to a human, a composition comprising a peptide D-Trp-Aib (SEQ ID NO: 30), wherein said composition is administered
   (a) orally, wherein the composition is formulated in the form of tablets, capsules, or liquid formulations;
   (b) parenterally, wherein the composition is formulated in the form of intraocular, intravenous, or subcutaneous direct injections; or
   (c) topically to the eye, wherein the composition is formulated in the form of an eye cream or an intraocular depot formulation;
wherein said administration inhibits Aβ formation and/or the occurrence of said Aβ toxicity in the eye of said human with glaucoma or AMD, and wherein said administration is effective for alleviation of the condition.

2. The method of claim 1, wherein glaucoma is selected from the group consisting of primary angle-closure glaucoma, secondary open-angle glaucoma, wide-angle glaucoma, steroid-induced glaucoma, traumatic glaucoma, secondary angle-closure glaucoma, and neovascular glaucoma.

3. The method of claim 1, wherein the composition comprising the peptide D-Trp-Aib (SEQ ID NO: 30) is co-administered to the human in combination with at least one additional pharmaceutical agent for treating the optical condition, wherein the combination of the composition comprising the peptide and the at least one additional pharmaceutical agent are effective in treating the condition.

4. The method of claim 3, wherein the at least one additional pharmaceutical agent is selected from the group consisting of anti-glaucoma drugs, antibiotics, anti-inflammatory drugs, steroids, anti-allergic drugs, and artificial tear fluid.

5. The method of claim 3, wherein the at least one additional pharmaceutical agent is selected from the group consisting of acetazolamide, diclofenamide, carteolol, timolol, metipranolol, betaxolol, pindolol, levobunolol, brimonidine, clonidine, pilocarpine, carbachol, dipivefrine, apraclonidine, brinzolamide, dorzolaminde, bimatoprost, travaprost, latanoprost, chlortetracycline, ciprofloxacine, ofloxacine, fusidinic acid, gentamicine, kanamycine, levofloxacine, lomefloxacine, oxytetracycline, natamycine, azidamfenicole, chloramphenicole, tobramycine, erythromycine, polymyxin-B, acaclovir, trifluridine, betamethasone, dexamethasone, fluorometholone, hydrocortisone, prednisolone, rimexolone, cromoglicate, azelastine, lodoxamide, emedastine, nedocromile, levocabastine, olopatadinea, ketotifene, hypromellose, carbomere, hyaluronate, carmellose, hypromellose, povidone, hyetellose, polivinylalcohole, dexpanthenole, tetryzoline, troxerutin, tramazoline, naphazoline, xylometazoline, phenylephrine and antazoline.

6. The method of claim 1, wherein the composition comprising the peptide is administered once a day, twice a day, or three times a day.

7. The method of claim 1, wherein the composition comprising the peptide is administered over an extended time period.

8. The method of claim 1, wherein when the composition comprising the peptide is administered in the form of an intraocular depot, administration comprises an application interval of 3-12 months.

9. The method of claim 1, wherein the formulation comprises an immediate or modified release formulation.

10. The method of claim 3, wherein the composition comprising the peptide and the at least one additional pharmaceutical agent are administered in a single formulation.

* * * * *

SEQUENCE LISTING

```
<160> NUMBER OF SEQ ID NOS: 33

<210> SEQ ID NO 1
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(3)
<223> OTHER INFORMATION: Stereoisomer D

<400> SEQUENCE: 1

Phe Phe Pro
1

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (2)..(3)
<223> OTHER INFORMATION: Stereoisomer D
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 2

Xaa Phe Asn Xaa
1

<210> SEQ ID NO 3
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(3)
<223> OTHER INFORMATION: Stereoisomer D

<400> SEQUENCE: 3

Phe Asn Pro
1

<210> SEQ ID NO 4
<211> LENGTH: 4
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 4

Xaa Asn Phe Xaa
1

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Gln Lys Leu Val Phe Phe
1               5

<210> SEQ ID NO 6
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 6

Tyr Tyr
1

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Stereoisomer D

<400> SEQUENCE: 7

Phe Phe Pro
1

<210> SEQ ID NO 8
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (2)..(3)
<223> OTHER INFORMATION: Stereoisomer D
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 8

Xaa Phe Asn Xaa
```

```
<210> SEQ ID NO 9
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)
<223> OTHER INFORMATION: Alpha-aminoisobutyric acid (Aib)

<400> SEQUENCE: 9

Xaa Asn Phe Xaa
1

<210> SEQ ID NO 10
<211> LENGTH: 2
<212> TYPE: PRT
<213> ORGANISM: Artificial Sequence
<220> FEATURE:
<223> OTHER INFORMATION: Synthetic Peptide

<400> SEQUENCE: 10

Tyr Tyr
1

<210> SEQ ID NO 11
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: amidated amino acid

<400> SEQUENCE: 11

Tyr Tyr
1

<210> SEQ ID NO 12
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)

<400> SEQUENCE: 12

Xaa Phe Phe
1

<210> SEQ ID NO 13
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
```

```
<222> LOCATION: (3)..(3)
<223> OTHER INFORMATION: Alpha-aminoisobutyric acid (Aib)

<400> SEQUENCE: 13

Asn Tyr Xaa
1

<210> SEQ ID NO 14
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 14

Asn Tyr Pro
1

<210> SEQ ID NO 15
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Beta-aminoisobutyric acid
<220> FEATURE:
<221> NAME/KEY: misc_feature
<222> LOCATION: (2)..(4)
<223> OTHER INFORMATION: Stereoisomer D

<400> SEQUENCE: 15

Xaa Pro Tyr Asn
1

<210> SEQ ID NO 16
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 16

Tyr Xaa
1

<210> SEQ ID NO 17
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

<400> SEQUENCE: 17

Pro Tyr
1
```

<210> SEQ ID NO 18
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

<400> SEQUENCE: 18

Tyr Pro
1

<210> SEQ ID NO 19
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 19

Asn Tyr Tyr Pro
1

<210> SEQ ID NO 20
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Alpha-aminoisobutyric acid (Aib)

<400> SEQUENCE: 20

Tyr Tyr Xaa
1

<210> SEQ ID NO 21
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)

<400> SEQUENCE: 21

Xaa Tyr Tyr
1

<210> SEQ ID NO 22
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Alpha-aminoisobutyric acid (Aib)
<220> FEATURE:
<221> NAME/KEY: misc_feature
<222> LOCATION: (4)..(4)

<223> OTHER INFORMATION: Alpha-aminoisobutyric acid (Aib)

<400> SEQUENCE: 22

Xaa Tyr Tyr Xaa
1

<210> SEQ ID NO 23
<211> LENGTH: 4
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D
<220> FEATURE:
<221> NAME/KEY: misc_feature
<222> LOCATION: (4)..(4)
<223> OTHER INFORMATION: Stereoisomer D

<400> SEQUENCE: 23

Asn Tyr Tyr Pro
1

<210> SEQ ID NO 24
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 24

Pro Tyr Tyr
1

<210> SEQ ID NO 25
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 25

Tyr Tyr Pro
1

<210> SEQ ID NO 26
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 26

Pro Tyr Tyr Pro
1

<210> SEQ ID NO 27
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

```
<400> SEQUENCE: 27

Tyr Tyr
1

<210> SEQ ID NO 28
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 28

Pro Xaa
1

<210> SEQ ID NO 29
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

<400> SEQUENCE: 29

Phe Pro
1

<210> SEQ ID NO 30
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D
<220> FEATURE:
<221> NAME/KEY: misc_feature
<222> LOCATION: (2)..(2)
<223> OTHER INFORMATION: Alpha-aminoisobutyric acid (Aib)

<400> SEQUENCE: 30

Trp Xaa
1

<210> SEQ ID NO 31
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(2)
<223> OTHER INFORMATION: Stereoisomer D

<400> SEQUENCE: 31

Trp Pro
```

```
<210> SEQ ID NO 32
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (1)..(1)
<223> OTHER INFORMATION: Stereoisomer D

<400> SEQUENCE: 32

Phe Pro
1

<210> SEQ ID NO 33
<211> LENGTH: 2
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (2)..(2)
<223> OTHER INFORMATION: Stereoisomer D

<400> SEQUENCE: 33

Pro Phe
1
```